LUNG VENTILATORS AND CONTROL MECHANISM THEREFOR
Original Filed Dec. 5, 1958 2 Sheets-Sheet 1
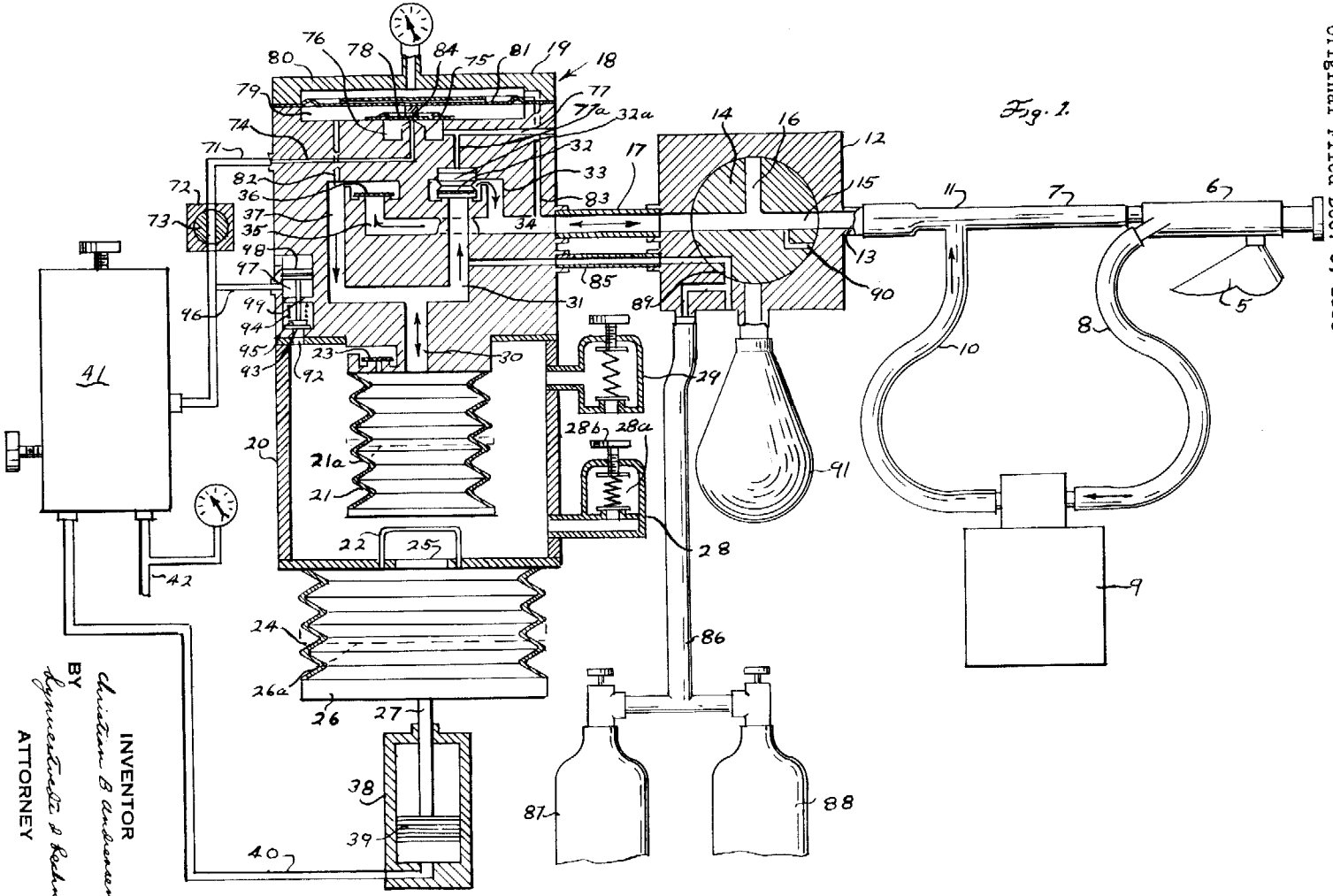
INVENTOR
Christian B. Andreasen
BY
Synnestvedt & Lechner
ATTORNEY

LUNG VENTILATORS AND CONTROL MECHANISM THEREFOR

Original Filed Dec. 5, 1958 2 Sheets-Sheet 2

INVENTOR
Christian B. Andreasen
BY
Symmes, West & Leckie
ATTORNEY

United States Patent Office

Re. 25,871
Reissued Oct. 5, 1965

25,871
LUNG VENTILATORS AND CONTROL MECHANISM THEREFOR

Christian B. Andreasen, New Hope, Pa., assignor to Air-Shields, Inc., Hatboro, Pa., a corporation of Delaware Original No. 3,046,979, dated July 31, 1962, Ser. No. 778,390, Dec. 5, 1958. Application for reissue June 21, 1963, Ser. No. 290,289
20 Claims. (Cl. 128—29)

Matter enclosed in heavy brackets [ ] appears in the original patent but forms no part of this reissue specification; matter printed in italics indicates the additions made by reissue.

This invention relates to lung ventilating devices suitable for use with anesthesia machine systems and is more particularly directed to improvements in the control mechanism for changing the pressure phases of the ventilating cycle including controls responsive to spontaneous respiration efforts.

Lung ventilators of the type to which the present invention is applicable are used to assist in the operation of breathing. Such machines normally have a breathing cycle which includes a positive pressure phase to assist inhalation and a negative phase to assist exhalation. Such ventilator devices are equipped with timing controls which regulate the period of the inhalation and exhalation phases. One of the objects of the present invention is to provide improved control mechanism with an additional control in the lung ventilator system which will switch the ventilator to the positive pressure phase immediately upon demand. Should the patient to which the equipment is attached initiate spontaneous respiration the resulting slight negative pressure developed in the system by the inhalation effort is utilized to immediately shift the ventilator to the positive pressure phase to assist the inhalation effort.

Another object of the invention is to provide improved equipment of this nature which may be used either strictly as a time cycled unit or as a system in which the timed cycle may be interrupted by a spontaneous respiration effort.

Still another object involves the provision of improved timing device construction with simplified valve control.

A further object of the invention is the provision of a lung ventilator drive system in which a source of gas under pressure provides the power for the drive of the ventilator to produce the positive and negative phases and at the same time this source of gas under pressure supplies the timing control to produce the change from positive to negative phase and vice versa. This object encompasses the provision of a valve controlled by a sensing diaphragm connected to the timing device to interrupt the normal timing function.

How these and other objects and advantages of the invention are accomplished will be clear from the following description of the drawing in which—

FIGURE 1 is a diagrammatic view of the lung ventilating and control apparatus of the present invention.

Figure 3:
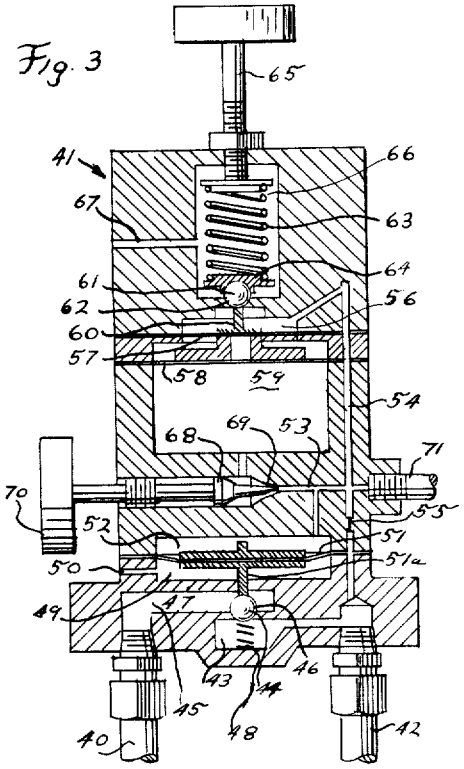
FIGURE 3 shows the timing control unit with the timing mechanism shifted to a different position from that shown in FIGURE 1.

Referring to the drawing FIGURE 1 shows a lung ventilating system in diagrammatic form. A mask 5 or other suitable applicator means is provided for applying the ventilating gas to the patient. Suitable valves are incorporated in the mask unit 6 so that the inhaled gas is supplied through the tube member 7. Exhaled gas is directed by means of the valving through tube 8 and through the cannister unit 9 for removal of the carbon dioxide. The remaining gas is then delivered back to the system through tube 10. A connecting tube 11 extends to the ventilator unit and connects to a valve 12 at its outlet 13.

As will be clearly seen the valve 12 incorporates a movable valve portion 14 having a through channel 15 and a branch channel 16. In the position shown in FIGURE 1 the branch channel 16 is ineffective and the through channel 15 joins the outlet 13 with channel 17 leading to the ventilator apparatus. The ventilator 18 incorporates a distributor head 19 to which the channel 17 is connected. The distributor 19 is supported at the upper side of a transparent walled chamber 20 in which is mounted a flexible walled or bellows unit 21 which can expand and contract from the full line position 21 to the dotted line position 21a. The fully expanded position of unit 21 is controlled by a suitable stop 22. A valve 23 permits bleeding of air from the inside of the bellows unit 21 through valve 23 into the chamber 20 at any time the pressure is lower in chamber 20 than inside bellows unit 21.

Another bellows 24 is attached to the underside of the chamber 20, the inside of bellows 24 being connected to the chamber by means of aperture 25 in the bottom of chamber 20. Bellows 24 has a weighted bottom disk 26 to which is attached connecting rod 27. The bellows 24 can move from extended position where the bottom 26 is in full line position to compressed position such as shown by dotted outline 26a. Thus bellows 24 forms a variable volume chamber which serves to produce a variable pressure in the chamber 20. The external pressure from chamber 20 is in turn impressed on the bellows unit 21. On the expansion stroke of the bellows 24 the weighted bottom causes a negative pressure to be developed in the chamber 20 and this negative pressure is also transmitted through bellows 21 into the ventilating system.

In order to control the magnitude of the positive or the negative pressure in the chamber 20 suitable relief valves are provided. Valve 28 permits bleeding of air from chamber 20 at a predetermined pressure and thus limits the value of positive pressure which can be transmitted to the ventilator system through the bellows unit 21. Valve 28 is adjustable by means of a spring 28a and a screw member 28b to vary the desired positive pressure setting within the limits suitable for operating the ventilating machine. Likewise the negative value of the pressure developed in chamber 20 can be controlled by valve 29 which permits entry of air through the valve upon reaching a predetermined differential value. Likewise valve 29 may be adjusted to provide the desired magnitude of negative pressure. With this construction the pressures developed in chamber 20 may be applied through the bellows unit 21 to the breathing gas system without admitting any of the gas from chamber 20 into the breathing gas.

Suitable connecting channels are provided between the ventilator bellows unit 21 and the ventilator delivery channel 17. Channel 30 leads from bellows 21 to an outgoing branch channel 31 which is connected by a one-way valve 32 beyond which a connecting channel 33 leads to channel 17. To transfer gas from the channel 17 to the bellows unit 21 it must pass from channel 17 through a channel 35, then through a one-way valve 36 after which it passes through a branch channel 37 and channel 30 to the bellows unit 21. The flow directions of the various channels are illustrated by means of suitable arrows it being noted that in certain sections such as channel 17 and channel 30 the flow may be in either direction while in other sections such as channels 31 and 33 and channels 35 and 37 flow is in one direction only due to the influence of the one-way valves 32 and 36. Attached to one-way valve 32 is a flexible bellows 32a to form a separate chamber above it.

Figure 2:
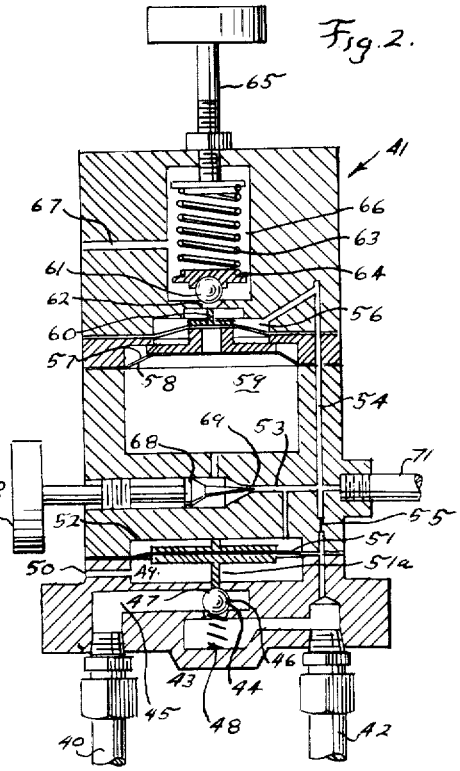
FIGURE 2 shows the timing control unit with the mechanism in position to match the positive phase operation corresponding to the position of the ventilator parts in FIGURE 1.

To actuate the bellows 24 to produce the positive and negative pressure phases in the system a cylinder 38 is equipped with a piston 39 attached to the connecting rod 27. A gas supply tube 40 leads from the timing control device 41 to the cylinder 38. A supply of air or other gas under pressure (e.g. 14 p.s.i.) is delivered to the timer device 41 by means of a pipe 42. By reference to FIGURE 2 it will be seen that the gas supply to tube 40 is transmitted from a chamber 43 past a valve member 44 to a channel 45. The valve member 44 is held off its seat 46 (FIGURE 2) and up against seat 47 by means of a spring 48. Above the seat 47 there is another chamber 49 which connects by means of aperture 50 to the outside atmosphere.

The upper side of the chamber 49 is formed by a flexibly mounted wall 51. Above the wall 51 is another chamber 52 which connects to channels 53 and 54. Channel 54 connects to the air supply pipe 42 and incorporates a restricting orifice 55. Channel 54 extends to join the valve chamber 56, the lower surface of which is a movable wall or diaphragm 57 which is attached to a movable wall structure 58 forming the upper surface of a control chamber 59. The area of the wall of chamber 59 is greater than that of the diaphragm 57 of chamber 56 so that when sufficient pressure is built up the wall 58 is moved upwardly and carries with it a rod 60 which lifts a valve member 61 off a seat 62. The valve 61 is normally held against the seat 62 by means of a valve spring 63 reacting against a valve contacting member 64. Thus the pressure area of wall 58 must be such that it can overcome the pressure in chamber 56 and also produce sufficient excess force to lift the valve 61 against the force of spring 63. Spring 63 can be adjusted to apply more or less force by means of an adjusting screw 65. A chamber 66 above the valve 61 is connected to the outer air by means of a channel 67. Thus when valve 61 is opened channel 54 is relieved to atmospheric pressure. The actual loss of gas is small because the restricting orifice 55 is quite small, the volume requirement of the timer being low in comparison to the volume requirement for driving the ventilator.

As previously mentioned FIGURE 1 shows the piston 39 and bellows 34 near the beginning of the positive pressure phase. As will be seen from the position of the parts in the timer 41, FIGURE 2, both the flexible wall 51 and the movable wall 58 are in their upper positions in which the upper valve 61 is open to relieve the pressure to atmospheric. Because the pressure in channel 54 and chamber 52 is atmospheric the valve member 44 admits gas under pressure from the supply pipe 42 to the tube 40 and thence to the cylinder 38 to actuate the bellows 24 during its pressure phase movement. To initiate this positive pressure phase the pressure in chamber 59 had built up by virtue of the bleeding of supply air into chamber 59 by way of a needle valve 68 and an orifice 69. The needle valve position is controlled by the knob 70 to increase or decrease the size of orifice 69 and thus the flow rate from the channel 53 to the chamber 59 to give the desired length of time for pressure build up in chamber 59. When the pressure has built up in chamber 59 to an amount somewhat below line pressure it causes the wall 58 to move upwardly and overcome the spring load 63 to open the valve 61 and release the pressure in channels 53 and 54 and chambers 52 and 56 to atmospheric. Releasing the pressure in chamber 52 causes the movable wall 51 and the attached rod 51a to move upwardly to permit the valve member 44 to raise from the seat 46 and allow the passage of the pressurized gas into the tube 40.

This timer valve condition exists at the beginning of the pressure stroke of cylinder 38 and continues during this phase. Since channels 53 and 54 are at atmospheric the pressure which has built up in chamber 59 causes reverse flow from the chamber 59 through orifice 69 into the channels 53 and 54 and through valve 61 to the atmosphere. This bleeding of air from chamber 59 continues until the pressure in 59 has lowered sufficiently so that the spring load 63 acting through the valve member 61 and the rod 60 causes the moving wall 58 to be pushed downwardly so that the valve 61 engages the seat 62. This position of the valve 61 is shown in FIGURE 3. As soon as valve 61 closes, the pressure immediately builds up in channels 53 and 54 and in chamber 52 to cause the wall 51 and rod 51a to move valve member 44 against the spring 48 and cause it to seat against the lower seat 46. In this position the upper orifice 47 is opened to the channel 45 and the pressure supply is cut off from the cylinder 38. Exhaust from the cylinder 38 may take place to the atmosphere by way of tube 40, channel 45, orifice 47, chamber 49 and orifice 50. This is the position of the parts of the timer during the negative phase operation of the timer during which time the weight of the bellows disk 26 causes the piston 39 to move downwardly in the cylinder 38 and causes the air to exhaust from the cylinder through the tube 40 and out to the atmosphere as noted.

During this negative phase operation there is flow from channel 53 which is now at line pressure into the chamber 59 past the needle valve 68. Flow in this direction gradually builds up the pressure in the chamber 59. When the pressure again reaches the critical point it causes movement of the wall 58 and opening of the valve 61 to relieve the pressure in the timer channels 53 and 54 and permit shifting of the lower valve 44 to the up position to initiate another positive phase of the cycle. By changing the pressure on spring 63 by means of the adjusting screw 65 the length of the negative phase can be changed with respect to the length of the positive phase. By adjusting the needle valve 68 through rotation of the knob 70 the time for increase and decrease of the pressure in chamber 59 may be adjusted to increase or decrease the length of the complete cycle. Thus by these two adjustments the cycle length may be changed or the phase relationship of the cycle may be varied while retaining the cycle time constant.

Figure 4:
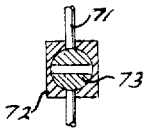
FIGURE 4 shows the manual valve in the connection between the spontaneous sensing valve and the timing device moved to closed position.

Referring again to FIGURES 1 and 2 it will be seen that a tube 71 connects the control device 41 with the distributor unit 19 of the ventilator device. Tube 71 connects into channel 54 of the timer device. A valve 72 having an internal member 73 permits closing the line 71 so that the connection between the timer device 41 and the ventilator is eliminated. The closed position of the valve 72 is shown in FIGURE 4 while FIGURE 1 shows the movable member 73 of the valve 72 in open position.

In the distributor unit 19 channel 74 connects to the tube 71 and extends to an outlet 75. The outlet of channel 74 normally opens into a small chamber 76 which is connected by channel 77 to the outside atmosphere. A diaphragm wall 78 forms the upper side of the small chamber 76. Above the diaphragm wall 78 is a chamber 79 and above chamber 79 is another chamber 80, the two chambers being separated by a flexibly mounted wall 81. A connecting channel 82 extends from the chamber 79 to the channel 37 which leads to the bellows unit 21. Another channel 83 extends from the upper chamber 80 to the anesthesia machine channel 17. Thus the lower chamber 79 is in direct connection with the bellows unit 21 while the upper chamber 80 is separated from the bellows 21 by the one-way valves 32 and 36.

A small projection 84 is supported on the lower side of the wall 81 in position to hold flexible wall 78 against the outlet of channel 74 to block it. During the negative phase there is a slight pressure differential due to the loss past valve 36. The slightly lower absolute pressure in bellows 21 causes wall 81 to be held in closed position. During the positive phase there is also a pressure difference between bellows unit 21 and channel 17 to cause flow past valve 32. This slight increase in pressure in chamber 79 causes opening of outlet 75 but under this condition timer valve 61 is also open. Inspiration continues until both outlet 75 and valve 61 are closed. The negative phase begins when flow past valve 32 ceases. During the negative phase of operation the downward motion of bellows 24 develops the negative pressure in the chamber 20 which is transmitted by the bellows unit 21 and through its expansion the negative pressure causes flow from the patient's lungs through the channel 17, the channel 35, past the valve 36 and through channel 37 to the bellows unit 21.

If during this negative pressure phase the patient attempts spontaneous inspiration, this causes in the channel 17 a negative pressure slightly greater in negative value than that being produced by the bellows 21. The inside of bellows 32a above valve 32 is connected by channels 77a and 77 to atmospheric pressure. Thus a negative pressure developed in channel 17 cannot open valve 32. As a result the greater negative pressure, that is, the lower absolute pressure in channel 17 produces a sufficient differential between chambers 79 and 80 so that the wall 81 is lifted to remove member 84 from flexible wall 78. This allows channel 74 to be opened through channel 77 to atmospheric pressure. This has the immediate effect of reducing the pressure in the timing device channels 53 and 54 to atmospheric with the result that both the lower valve 44 and the upper valve 61 move to their upper positions. Gas under pressure flows into the line 40 and causes the cylinder 38 to initiate a positive pressure stroke of the ventilator. Thus the ventilator responds immediately to the patient's effort and produces a positive pressure to assist the spontaneous inspiration. When the cycle is changed by the patient's inspiration the gas under pressure in chambers 52 and 56 is exhausted to atmosphere through channel 77 in a fashion which gives an audible indication that the patient has initiated the cycle, The positive pressure phase continues until the timer unit valve 61 and the outlet 75 have closed to demand the negative phase.

A separate channel 85 is provided leading to the ventilator channel 31. Channel 85 connects through the valve 12 by means of a tube 86 with suitable sources of supply, illustrated at 87 and 88, of breathing gas which may include an anesthesia gas and oxygen or additional gases when desired. Flowing the breathing gas at a point between bellows unit 21 and valve 32 prevents loss of sensitivity to the effort of the patient to inspire and thus improves the response of the apparatus.

Figure 5:
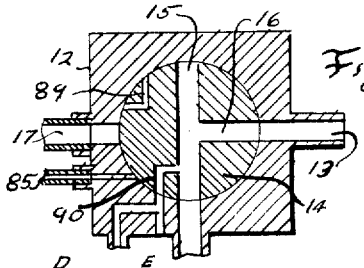
FIGURE 5 shows the manually controlled valve in the channel connection leading to the patient turned to manual position.

It will be noted that when the valve 12 is in the position shown in FIGURE 1 the breathing gas is connected to the channel 85 through the valve channel 89. However when the valve 12 is rotated to the position shown in FIGURE 5 the connection to the mechanical ventilator machine is shut off and the valve channel 16 connects the breathing bag 91 to the patient. In this position a valve channel 90 connects the breathing gas supply with the delivery channel 15, 16. Thus the system can be switched from automatic operation to manual when desired.

Another improvement in the ventilator apparatus is shown in FIGURE 1 where a special relief valve device is connected with the variable pressure chamber 20. An outlet orifice 92 is provided with a one-way valve member 93 which is held down by spring 94 reacting against a flange 95 which engages the valve member 93. The valve chamber above valve member 93 is open to the outside atmosphere.

Connected to tube 71 from the timer 41 is a tube 96 leading to chamber 97 in which is mounted a piston 98. Piston rod 99 connects piston 98 with the flange 95. The portion of chamber 97 above piston 98 is open to the atmosphere.

From the previous description of the timer operation the pressure in channel 54 and thus tube 71 is released to atmospheric during the positive pressure phase of the ventilating cycle. As a result the pressure both above and below piston 98 is atmospheric so that the spring 94 is effective in holding the valve member 93 on its seat. Upon closing of the timer valve 61 at the end of the positive pressure phase the pressure in channels 71, 96 and chamber 97 causes the piston 98 to rise thus leaving the valve member 93 free to open in response to pressure above atmospheric in chamber 20. Thus for a brief instant at the end of the positive pressure phase some of the gas from chamber 20 can escape through valve 93. Escape in this fashion lasts only until the bellows 24 has moved sufficiently to create a negative pressure in chamber 20.

Escape of this gas to the atmosphere has the effect of bringing the negative phase more quickly because less stroke is required to change the compressed gas in chamber 20 to expanded gas. The bleeding of gas through valve 98 gives an effective increase in capacity for the bellows 24 during the negative phase. This valve also provides an improved method of bleeding off excess gas fed to the ventilator system and which overflows to chamber 20 from bellows unit 21 by way of the overflow valve 23. If desired to shut off this auxiliary bleeder valve system the shut-off valve 72 may be located in tube 71 at a point between connecting tube 96 and the timer 41.

Figure 6:
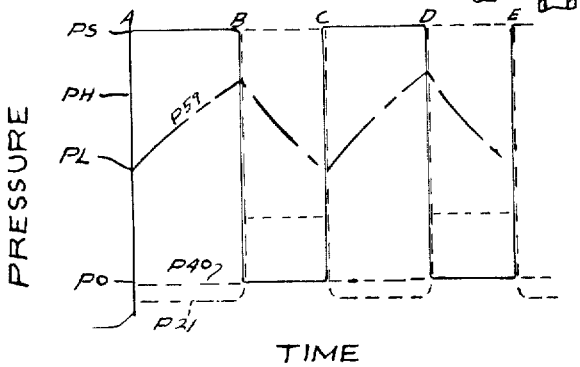
FIGURE 6 is a pressure diagram showing the relationship of pressure variation in various parts of the apparatus during operation.

The general pressure relationships are illustrated in the diagram in FIGURE 6 although the relative pressure values shown are not necessarily to scale. Atmospheric pressure is represented by Po while the pressure of the supply line 42 is Ps. Solid line P54 is the pressure curve for channel 54 which is the same pressure as valve chambers 52 and 56. Dash line P40 represents the pressure in the tube 40 leading to the drive cylinder 38. Broken line P59 shows the variation of pressure in the control chamber 59 of the timer and varies from a value PL to a higher value PH. These values may be varied by adjusting spring 63. The dotted line P21 represents the pressure in the ventilator system as transmitted by bellows unit 21.

Thus at point A of the diagram a negative pressure phase is beginning. Full line pressure Ps is applied to the timer since upper valve 61 is closed. This results in lower valve 44 closing off line pressure to the drive with the result that tube 40 is exhausting to atmospheric pressure, Po. This allows the drive bellows 24 to be expanding and thus causing a negative pressure in bellows 21 as shown by dotted line P21 which is below atmospheric pressure. During the time interval from A to B the pressure in control chamber 59 is gradually increasing as shown by P59.

When the pressure P59 reaches PH value the valve 61 opens. Thus at position B, FIGURE 6, the pressure in channel 54 falls to atmospheric Po with the result that lower valve 44 opens to admit pressure to tube 40. Thus the value of P40 immediately increases to Ps and the piston 39 causes a pressure phase to develop in bellows unit 21. Thus between B and C curve P21 is at a positive pressure, this being the pressure phase of the cycle. During this period from B to C the chamber pressure P59 reduces till it reaches pressure PL when valve 61 again closes to start another negative pressure phase.

The vertical portions of curves P54 and P40 are shown slightly displaced for clarity. Actually these lines should be superimposed.

From the foregoing it will be evident that I have provided an improved lung ventilator control. The arrangement of valves provides a simple and reliable control for applying and shutting off the ventilator driving energy. The use of a valve having a double seat and double function, combined with a pressure control to shut off flow of gas under pressure, helps to give improved operation with a simpler mechanism. By introducing the auxiliary control initiated by pressure changes in the ventilator system by efforts at spontaneous inhalation on the part of the patient the usefulness of the apparatus is further increased. This feature eliminates the "bucking" tendency when natural respiration occurs, the apparatus responding in a fashion which assists the patient with attempts at natural respiration. The auxiliary bleed valve of the variable pressure chamber further adds to the quality and efficiency of operation. Delivery of the breathing gas into the system between the bellows unit and the one-way valve gives adequate sensitivity to assure reliable spontaneous respiration control.

I claim:

1. Lung ventilation apparatus having a delivery system for supplying breathing gas to a patient, pressure applying means for applying alternate positive and negative pressure phases to the system, a controller having a connection to said pressure applying means for changing the phase from positive to negative and vice versa, said controller having a supply of pressure gas thereto for actuating purposes, a valve in said controller to release the controller pressure to atmospheric during the positive phase of operation of the ventilating apparatus, an auxiliary control for causing a change from negative to positive pressure application in response to a negative pressure induced in the delivery system by attempted spontaneous respiration on the part of the patient, said auxiliary control including a pressure responsive member and a valve, said pressure responsive member being connected to said delivery system and said valve having a connection to said controller, and a connection to the atmosphere to permit release of the controller pressure to atmospheric in response to spontaneous inhalation.

2. Lung ventilating apparatus constructed in accordance with claim 1 in which a shut off valve is provided in the connection between the auxiliary control and the controller to allow operation either as a direct pressure applied ventilator or as an assister ventilator responsive to spontaneous respiration pressures.

3. Lung ventilating apparatus including a breathing gas conveying system, a pressure varying container connected to one end of said system, a portion of said system adjacent said container having a branch channel with a one-way valve for conveying gas moving from said container and another branch channel with a one-way valve for conveying gas moving to said container, a main channel in said system to which said branch channels connect, a timing device having operative connections to said container for controlling the application of negative and positive pressure and thus the direction of flow to and from said container, said timing device being actuated by a pressure gas supply thereto, a control valve in said timing device movable to release the gas in said timing device to atmospheric pressure, means responsive to the change to atmospheric to induce a positive pressure application to the breathing gas system, an auxiliary control for said timing device including a pressure actuated wall member, a channel leading to one side of said wall member from one of said branch channels at a point between said container and said one way valve, a connection from the other side of said wall member to said main channel, a valve device operated by said pressure actuated member and a connection from said timing device to the atmosphere controlled by said valve device thereby causing said timing device to induce a positive pressure application to the breathing gas system in response to a negative pressure applied to said pressure actuated wall member by reduced pressure in said main channel caused by spontaneous inhalation.

4. Lung ventilating apparatus having a channel system for delivering breathing gas to a patient, a flexible walled chamber connected to said channel system, a variable pressure chamber in which said flexible walled chamber is mounted, a timing device for controlling the pressure in said variable pressure chamber from a positive pressure to a negative pressure and vice versa, said timing device being connected with a supply of gas under constant pressure, interconnecting means between said timing device and said variable pressure chamber, said means including a channel leading from said timing device, a first valve mounted in said timing device to intermittently permit flow of gas out of said device through said channel leading therefrom and then close off the flow, bias means urging said valve to gas flow position, a pressure responsive wall in said timing device having a member engageable with said valve to move it against said bias means to close off the flow, a second valve in said timing device having internal connections to control said first valve, a control chamber having a movable wall with a connection to said second valve to control its movements, a channel leading from said second valve to the atmosphere, opening of said second valve causing release of pressure on said pressure responsive wall to permit opening of said first valve to allow flow of gas through said channel leading from said timing device and closing of said second valve causing pressure build up at said pressure responsive wall to close said first valve against flow of said pressure gas.

5. Lung ventilating apparatus having a variable pressure chamber, a flexible walled container supported in said chamber, an applicator for administering breathing gas to a patient, a breathing gas conveying system between said container and said applicator, said system including a portion adjacent said container having two branch channels, a one-way valve mounted in each of said branch channels, a main channel into which said branch channels connect, the one-way valve in the first of said branch channels providing only for flow from said container to said main channel, the one-way valve in the second of said branch channels providing only for flow from said main channel to said container, a flexibly mounted diaphragm wall supported in said apparatus, a connecting channel extending from one of said branch channels at a point between said container and one of said one-way valves to one side of said diaphragm wall, another connecting channel extending from the said main channel to the other side of said diaphragm wall, a timing device operated by gas pressure, said timing device having operative connections to said variable pressure chamber for controlling the change of pressure in the chamber, a valve in said timing device to release the gas pressure therein to atmospheric to initiate one phase of the control, a channel connection from said timer to the atmosphere, a control member in said channel connection actuated by said diaphragm wall to open and close said channel connection.

6. Lung ventilating apparatus having mechanism actuated by a supply of gas under pressure, a timing device to control admission of gas to the actuating mechanism and release of gas therefrom, said device having a channel connecting it to said actuating mechanism, a valve member in said device, bias means normally urging said valve member to gas admission position, a pressure actuated diaphragm having a connection to said valve member to move it against said bias means to shut off gas flow to said actuating mechanism, said timing device including a second valve opening to atmosphere, said second valve having means to normally urge it to closed position, a control chamber having a movable wall with a connection to actuate said second valve, a channel structure in said timing device having a restrictive orifice connecting it to said source of pressure gas, said channel structure having connections to said diaphragm, said second valve and said control chamber, the connection to said control chamber being through an adjustable restrictive orifice, said movable wall causing opening of said second valve under application of pressure build up in said control chamber, opening of said second valve causing release of pressure in said channel structure to permit opening of said first valve to admit pressure gas to said actuating mechanism, release of pressure in said channel structure also permitting flow of gas from said control chamber to cause gradual pressure reduction, changing the adjustment of the restrictive orifice causing variation in the timing of the lung ventilating actuating mechanism.

7. Lung ventilating apparatus in accordance with claim 6 in which said actuating mechanism incorporates a channel connected to said channel structure in said timing device, said channel extending to the atmosphere, a third control valve connected to said channel to control opening and closing it to atmosphere, said third valve having control means connected to the lung ventilating apparatus, said control means being actuated under the influence of negative pressures induced by inhalation efforts of a patient.

8. Lung ventilating apparatus having a variable pressure chamber, powered mechanism connected to said variable pressure chamber to produce a positive pressure phase therein and a negative pressure phase, a separate chamber having a flexible wall mounted in said variable pressure chamber, a breathing gas applicator, connecting means leading from said separate chamber to said applicator, said connecting means incorporating a main conducting channel and two short connecting channels, a one-way valve mounted in each of said connecting channels, one of said connecting channels and its one-way valve providing for flow from said separate chamber to said main channel, the other of said connecting channels and its one-way valve providing for flow from said main channel to said separate chamber, a pair of chambers separated by a flexible diaphragm, a channel leading from said separate chamber to one side of said diaphragm, another channel connecting the other side of said diaphragm to said main channel, a timing device having a connection to said powered mechanism and having a control therein operable to change the variable pressure chamber from negative pressure to positive pressure, said control having means responding to release of gas pressure to atmospheric pressure to initiate a positive pressure phase, a gas flow channel extending from said timing device to the atmosphere, a shut-off control in said gas flow channel having an operating connection to said diaphragm, said diaphragm being movable by differential pressure thereon to cause said shut-off control to open said channel to atmospheric thereby actuating said timing device to initiate a positive pressure phase.

9. Lung ventilating apparatus having a channel system for delivering breathing gas to a patient, a flexible walled chamber connected to said channel system, equipment having operative connections with said flexible walled chamber for alternating the pressure in said flexible walled chamber from a pressure above atmospheric to a pressure below atmospheric, a timing control device for said equipment, said device having a supply line connected to it for delivering gas under pressure, a delivery line leading from said device to said equipment, a channel in said device connected to said delivery line, said channel having a first opening to connect it to said delivery line, said channel having a second opening to connect it to the outside of said device, a valve member located in said channel having bias means to move it to block the second of said openings during above atmospheric operation, and a pressure actuated diaphragm having means engageable with said valve member to move it against said bias means to block the first of said openings during the period of operation below atmospheric pressure.

10. A timing control device for a lung ventilator to control the periodic delivery of gas under pressure to the ventilator and the release of gas therefrom, said device having a supply line connected to for delivering gas under pressure, a delivery line attached to and leading from said device, a channel in said device connected to said delivery line, a first opening between said supply line and said channel, a second opening between said channel and the outside atmosphere, a valve member having a spring to move it to block said second opening, a movable wall supported adjacent said second opening and having a part engageable with said valve to move it to block said first opening, a control chamber in said timing device having a connection with said movable wall, a channel in said timing device extending between said control chamber and said supply line, said channel having a restrictive orifice therein, a relief valve assembly in said timing device having a connection to said control chamber channel, said valve assembly having an operative connection with said control chamber and being movable thereby to open position to connect said last mentioned channel to atmosphere.

11. Lung ventilating apparatus having a delivery system for supplying breathing gas to a patient, a pressure varying chamber connected to said system, said system having a main delivery channel, a branch channel extending between said chamber and said main channel and having a one-way valve to allow flow from said main channel to said chamber, a second branch channel extending between said chamber and said main channel and having a one-way valve to allow flow only from said chamber to said main channel, said last mentioned one-way valve having a flexible walled structure connected thereto to form a small chamber, a vent connecting said small chamber to the outside atmosphere, a timing control device having operative connections to change the pressure in said pressure varying chamber from a positive pressure phase to a negative pressure phase and vice versa, a movable wall member in said apparatus, a chamber on each side of said wall member, a connecting passage from the chamber on one side of said wall member to the first branch channel leading to said pressure varying chamber, a connecting passage from the chamber on the other side of said movable wall member leading to said main channel, said timing control device having a venting valve therein which when opened causes initiation of a positive pressure phase to said pressure varying chamber, a connecting line extending from said timing control device to a point adjacent said movable wall member and means actuable by said movable wall member to control the venting of said connecting line to atmospheric thereby providing an alternate means for initiating a positive pressure phase to said pressure varying chamber.

12. Lung ventilating apparatus having a variable pressure chamber, a flexible walled chamber mounted inside said variable pressure chamber, a breathing gas system connected to said flexible walled chamber, pressure varying means connected to said variable pressure chamber to provide a positive pressure phase and a negative pressure phase, a timing control device connected to said pressure varying means, said timing device having a connection to a source of pressurized gas, an interal control channel in said timing device having valve means to open said channel to atmosphere, closing of said valve means causing a pressure increase above atmospheric in said internal control channel, said pressure varying means having operative connections to induce negative pressure in said variable pressure chamber when said valve means is closed, and a relief valve device connected to said variable pressure chamber having a valve member and a pressure actuated valve control having a channel connection to the internal control channel of said timing control device.

13. Lung ventilating apparatus in accordance with claim 12 in which said relief valve device incorporates a spring which holds said valve member closed when positive pressure is present in said variable pressure chamber and a piston releases the spring pressure when the phase changes to the negative phase thereby permitting momentary release of gas during the change from positive to negative pressure in said variable pressure chamber.

14. Lung ventilating apparatus having a variable pressure chamber, a channel system for delivering breathing gas connected to said chamber, said system including a main delivery channel and a plurality of one-way valves located between said chamber and said main channel, control equipment connected to said variable pressure chamber to vary the pressure in said chamber including a device for producing a timed cycle, means for supplying pressure gas to said device and valve means to release gas pressure in said device to atmospheric, an auxiliary control for interrupting a timed cycle in response to induced pressures in said main channel, said auxiliary control having a control channel connected into said device for producing a timed cycle and leading to the atmosphere, a pressure responsive member in said auxiliary control, a control channel therefor leading from said main channel, to said auxiliary control, means attached to said pressure responsive member to open and close said control channel leading from said timed cycle device to the atmosphere.

15. Lung ventilating apparatus having a variable pressure chamber, a channel system for delivering breathing gas connected to said chamber, said system having a main delivery channel and a branch channel having a one-way valve controlling flow from said main channel to said chamber, a second branch channel having a one-way valve controlling flow from said chamber to said main channel, a control device having operative connections to said variable pressure chamber to control the pressure therein, said device being supplied with gas under pressure and being regulated by release of pressure, a pressure responsive movable wall having one side connected to said main dedelivery channel, a relief channel leading from said control device, means movable by said movable wall to open and close said relief channel and a connection for conveying breathing gas into said channel system, said connection entering said system at a point separated from said main delivery channel by said one-way valves.

16. Lung ventilating apparatus in accordance with claim 15 in which said main channel includes a switching valve, a manually operable breathing bag connectible through said switching valve, said connection for conveying breathin gas extending through said switching valve, said switching valve including a control channel to direct said connection for breathing gas into said main channel when said switching valve is moved to connect the manually operable breathing bag.

*17. Lung ventilating equipment comprising a channel system for delivering breathing gas to a patient, power means for developing pressure in said channel system to effect inhalation by the patient and including a fluid pressure supply valve and a fluid pressure sensitive actuating device for the supply valve having a control chamber and responsive to a pressure drop in said control chamber to open the supply valve, mechanism for controlling the pressure in said control chamber including means for introducing pressure fluid to effect closure of the supply valve and including two vent passages each arranged to vent said control chamber to effect opening of the supply valve and each having a vent valve therein, a timer device for periodically opening and closing one of said vent valves, and a device responsive to inhalation effort by the patient for opening the other of said vent valves.*

*18. Lung ventilating equipment comprising a channel system for delivering breathing gas to a patient, power means for developing pressure in said channel system to effect inhalation by the patient and including a fluid pressure supply valve and a fluid pressure sensitive actuating device for the supply valve having a control chamber and responsive to a pressure drop in said control chamber to open the supply valve, mechanism for controlling the pressure in said control chamber including means for introducing pressure fluid to effect closure of the supply valve and including two vent passages each arranged to vent said control chamber to effect opening of the supply valve and each having a vent valve therein biased to closed position, a timer device for periodically opening one of said vent valves and a device responsive to inhalation effort by the patient for opening the other of said vent valves.*

*19. Lung ventilating equipment comprising a patient's supply system including a channel for delivering breathing gas to the patient and a bellows with its interior in communication with said channel, a chamber surrounding the bellows, power means for developing pressure in said chamber to thereby collapse the bellows and effect inhalation by the patient, the power means including a fluid pressure supply valve for delivering pressure fluid into said chamber and further including a fluid pressure sensitive actuating device for the supply valve having a control chamber and responsive to a pressure drop in said control chamber to open the supply valve, mechanism for controlling the pressure in said control chamber including means for introducing pressure fluid to effect closure of the supply valve and including two vent passages each arranged to vent said control chamber to effect opening of the supply valve and each having a vent valve therein, a timer device for periodically opening and closing one of said vent valves, and a fluid pressure device having a control connection communicating with the patient's supply system and responsive to reduction in pressure in said system under the influence of inhalation effort by the patient to open the other of said vent valves.*

*20. Lung ventilating equipment comprising, in combination with a source of pneumatic pressure fluid, a patient's supply system including a channel for delivering breathing gas to the patient and a bellows with its interior in communication with said channel, a chamber surrounding the bellows, power means for developing pressure in said chamber to thereby collapse the bellows and effect inhalation by the patient, the power means including a fluid pressure supply valve for delivering pressure fluid from said source into said chamber and further including a fluid pressure sensitive actuating device for the supply valve having a control chamber and responsive to a pressure drop in said control chamber to open the supply valve, mechanism for controlling the pressure in said control chamber including means for introducing pressure fluid from said source to effect closure of the supply valve and including two vent passages each arranged to vent said control chamber to effect opening of the supply valve and each having a vent valve therein, a timer device for periodically opening and closing one of said vent valves, and a fluid pressure device having a control connection communicating with the patient's supply system and responsive to reduction in pressure in said system under the influence of inhalation effort by the patient to open the other of said vent valves.*

References Cited by the Examiner

The following references, cited by the Examiner, are of record in the patented file of this patent or the original patent.

UNITED STATES PATENTS

| | | | |
|---|---|---|---|
| 2,547,458 | 4/51 | Goodner | 128—29 |
| 2,591,120 | 4/52 | Blease | 128—29 |
| 2,737,178 | 3/56 | Fox | 128—29 |
| 2,867,210 | 1/59 | Bennett | 128—29 |
| 2,904,035 | 9/59 | Andreasen | 128—29 |

FOREIGN PATENTS

| | | |
|---|---|---|
| 1,017,808 | 10/52 | France. |

RICHARD A. GAUDET, *Primary Examiner.*